United States Patent [19]

Medabalimi

[11] Patent Number: 5,872,210
[45] Date of Patent: Feb. 16, 1999

[54] TRANSFRAME PEPTIDE INHIBITOR OF VIRAL PROTEASE

[75] Inventor: John L. Medabalimi, Olney, Md.

[73] Assignee: The United States of America as represented by the Department of Health and Human Services, Washington, D.C.

[21] Appl. No.: 539,432

[22] Filed: Oct. 5, 1995

[51] Int. Cl.[6] .......................... A61K 38/04; A61K 39/42; C07K 5/00; C07H 21/02

[52] U.S. Cl. .......................... 530/327; 530/328; 530/329; 530/330; 424/160.1; 424/208.1; 536/23.1; 536/23.53

[58] Field of Search .............................. 424/160.1, 208.1; 530/328, 327, 329, 330; 536/23.1, 23.53

[56] References Cited

U.S. PATENT DOCUMENTS

| | | | |
|---|---|---|---|
| 5,087,557 | 2/1992 | McClure | 435/5 |
| 5,188,950 | 2/1993 | Balani et al. | 435/120 |
| 5,245,015 | 9/1993 | Fung et al. | 530/388.35 |
| 5,342,922 | 8/1994 | Marshall et al. | 530/329 |

FOREIGN PATENT DOCUMENTS

| | | |
|---|---|---|
| 0 498 784 A2 | 8/1992 | European Pat. Off. . |
| 43 32395 A1 | 4/1995 | Germany . |
| WO 88/09815 | 12/1988 | WIPO . |
| WO 91/13904 | 9/1991 | WIPO . |
| WO 95/27054 | 10/1995 | WIPO . |

OTHER PUBLICATIONS

Szewczuk, A., et al., "Specificity of γ–Glutamyl Cyclotransferase", *Can. J. Biochem.*, 53:706–712 (1975).

Szewczuk, A., et al., "Specificity of γ–Glutamyl Cyclotransferase", Chemical Abstracts, vol. 83, abstract No. 92952 (1975).

Yamamoto, Y., et al., "Synthesis of Hexatriacontapeptide Amide Corresponding to the Proposed Structure of Neuropeptide Y (NPY)", *Peptide Chemistry*, 317–322 (1985).

Yamamoto, Y., et al. "Synthesis of Hexatriacontapeptide Amide Corresponding to the Proposed Structure of Neuropeptide Y (NPY)", Chemical Abstracts, vol. 103, abstract No. 123894 (1985).

Cason, J., et al. "Identification of Immunogenic Regions of the Major Coat Protein of Human Papillomavirus Type 16 that Contain Type–restricted Epitopes" *J. Gen. Virol.*, 70:2973–2987 (1989).

Cason, J., et al. "Identification of Immunogenic Regions of the Major Coat Protein of Human Papillomavirus Type 16 that Contain Type–restricted Epitopes", Chemical Abstracts, vol. 112, abstract No. 116820 (1989).

Slootstra, J., et al., "Structural aspects of antibody–antigen interaction revealed through small random peptide libraries", *Molecular Diversity*, 1:87–96 (1995).

Slootstra, J., et al., "Structural aspects of antibody–antigen interaction revealed through small random peptide libraries", Chemical Abstracts, vol. 124, abstract No. 257898.

Robinson, Michael B., et al., "Hydrolysis of the Brain Dipeptide N–Acetyl–L–aspartyl–L–glutamate", *The Journal of Biological Chemistry*, 262:14498–14506 (1987).

(List continued on next page.)

*Primary Examiner*—Jeffrey Stucker
*Assistant Examiner*—Hankyel T. Park
*Attorney, Agent, or Firm*—Morgan & Finnegan, L.L.P.

[57] ABSTRACT

The present invention describes small, water soluble peptides isolated from a native virus inhibitory sequence that blocks maturation of the virally encoded protease and inhibits the mature protease as well. The peptides may be used in the treatment of virally infected cells, in the preparation of vaccine formulations, in the generation of clinically relevant antibodies and anti-idiotypic antibodies and in the generation of a screening assay or kit that can be used to identify other similarly acting protease inhibitors.

10 Claims, 3 Drawing Sheets

OTHER PUBLICATIONS

Anderson, D.C., et al. "Exact Definition of Species–Specific and Cross–Reactive Epitopes of the 65–kilodalton Protein of Mycobacterium leprae Using Synthetic Peptides", *The Journal of Immunology*, 141:607–613 (1988).

Battle, J.K., et al. "Immunological Characterization of the gag Gene Products of Bovine Immunodeficiency Virus," *Journal of Virology*, 66:6868–6877 (1992).

Zybarth, G., et al., "Domains Upstream of the Protease (PR) in Human Immunodeficiency Virus Type 1 Gag–Pol Influence PR Autoprocessing", *Journal of Virology*, 69:3878–3884 (1995).

Giam, Chou–Zen, et al. "In Vivo and in Vitro Autoprocessing of Human Immunodeficiency Virus Protease Expressed in *Escherichia coli*," The Journal Biological Chemistry, 263: 14617–14620 (1988).

Strickler, James E., et al. "Characterization and Autoprocessing of Precursor and Mature Forms of Human Immunodeficiency Virus Type (HIV 1) Protease Purified From *Escherichia coli*", *Proteins: Structure, Function and Genetics*, 6:139–154 (1989).

Louis, J. L., et al. "Autoprocessing of the HIV–1 protease using purified wild–type and mutated fusion proteins expressed at high levels in *Escherichia coli*", *Eur. J. Biochem.* 199, 361–369 (1991).

Reil, H., et al. "A Heptanucleotide Sequence Mediates Ribosomal Frameshifting in Mammalian Cells", *Journal of Virology*, 67:5579–5584, (1993).

Zybarth, Gabrielle, et al. "Proteolytic Activity of Novel Human Immunodeficiency Virus Type 1 Proteinase Proteins from a Precursor with a Blocking Mutation at the N Terminus of the PR Domain", *Journal of Virology*, 68:240–250 (1994).

Louis, John M., et al. "Kinetics and mechanism of autoprocessing of human immunodeficiency virus type 1 protease from an analog of the Gag–Pol polyprotein", *Proc. Nat'l Acad. Sci.*, 9:7970–7974 (1994).

Wondrak, Ewald M., et al. "Removal of Zinc is Required for Processing of the Mature Nucleocapsid Protein of Human Immunodeficiency Virus, Type 1, by the Viral Protease", *The Journal of Biological Chemistry*, 269: 21948–21950 (1994).

Miller, Michael D., et al. "Advances in Automated Docking Applied to Human Immunodeficiency Virus Type 1 Protease", *Methods in Enzymology*, 241: 354–70 (1994).

Ringe, D., "X–Ray Structures of Retroviral Proteases and Their Inhibitor–Bound Complexes", *Methods in Enzymology*, 241:157–177 (1994).

Vacca, J. P., "Design of Tight–Binding Human Immunodeficiency Virus Type 1 Protease Inhibitors", *Methods in Enzymology*, 241:311–334 (1994).

Kempf, D.J., "Design of Symmetry–Based, Peptidomimetic Inhibitors of Human Immunodeficiency Virus Protease", *Methods in Enzymology*, 241:334–354 (1994).

Balani, S.K., et al. "Metabolism of L–689,502 by Rat Liver Slices to Potent HIV–1 Protease Inhibitors", *Drugs Metabolism and Disposition*, 23:185–189 (1995).

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
        ( A ) LENGTH: 8
        ( B ) TYPE: Amino Acid
        ( C ) STRANDEDNESS: Single
        ( D ) TOPOLOGY: Linear     ( x i ) SEQUENCE DESCRIPTION: SEQ ID NO: 1:

Phe Leu Arg Glu Asp Leu Ala Phe
1               5

( 2 ) INFORMATION FOR SEQ ID NO: 2:

( i ) SEQUENCE CHARACTERISTICS:
        ( A ) LENGTH: 6
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 2:

Gly Glu Asp Leu Ala Phe
1               5

( 2 ) INFORMATION FOR SEQ ID NO: 3:

( i ) SEQUENCE CHARACTERISTICS:
        ( A ) LENGTH: 4
        ( B ) TYPE: Amino Acid
        ( C ) STRANDEDNESS: Unknown
        ( D ) TOPOLOGY: Linear ( x i ) SEQUENCE DESCRIPTION: SEQ ID NO: 3:

Glu Asp Leu Ala
 1

( 2 ) INFORMATION FOR SEQ ID NO: 4:

( i ) SEQUENCE CHARACTERISTICS:
        ( A ) LENGTH: 3
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 4:

Glu Asp Leu
 1

( 2 ) INFORMATION FOR SEQ ID NO: 5:

( i ) SEQUENCE CHARACTERISTICS:
        ( A ) LENGTH: 3
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 5:

Arg Glu Asp
 1

( 2 ) INFORMATION FOR SEQ ID NO: 6:

( i ) SEQUENCE CHARACTERISTICS:
        ( A ) LENGTH: 4
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 6:

Asp Leu Ala Phe
 1

( 2 ) INFORMATION FOR SEQ ID NO: 7:

( i ) SEQUENCE CHARACTERISTICS:
        ( A ) LENGTH: 3
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 7:

Asp Glu Leu
 1

( 2 ) INFORMATION FOR SEQ ID NO: 8:

( i ) SEQUENCE CHARACTERISTICS:
        ( A ) LENGTH: 3
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 8:

Glu Glu Leu
 1

( 2 ) INFORMATION FOR SEQ ID NO: 9:

( i ) SEQUENCE CHARACTERISTICS:

(A) LENGTH: 3
                (B) TYPE: Amino Acid
                (C) STRANDEDNESS: Unknown
                (D) TOPOLOGY: Linear (xi) SEQUENCE DESCRIPTION: SEQ ID NO: 9:

Asp Asp Leu
 1

(2) INFORMATION FOR SEQ ID NO: 10:

(i) SEQUENCE CHARACTERISTICS:
                (A) LENGTH: 3
                (B) TYPE: Amino Acid
                (C) STRANDEDNESS: Unknown
                (D) TOPOLOGY: Linear (xi) SEQUENCE DESCRIPTION: SEQ ID NO: 10:

Glu Asn Leu
 1

(2) INFORMATION FOR SEQ ID NO: 11:

(i) SEQUENCE CHARACTERISTICS:
                (A) LENGTH: 3
                (B) TYPE: Amino Acid
                (C) STRANDEDNESS: Unknown
                (D) TOPOLOGY: Linear (xi) SEQUENCE DESCRIPTION: SEQ ID NO: 11:

Glu Lys Phe
 1

(2) INFORMATION FOR SEQ ID NO: 12:

(i) SEQUENCE CHARACTERISTICS:
                (A) LENGTH: 3
                (B) TYPE: Amino Acid
                (C) STRANDEDNESS: Unknown
                (D) TOPOLOGY: Linear (xi) SEQUENCE DESCRIPTION: SEQ ID NO: 12:

Glu Asp Phe
 1

(2) INFORMATION FOR SEQ ID NO: 13:

(i) SEQUENCE CHARACTERISTICS:
                (A) LENGTH: 3
                (B) TYPE: Amino Acid
                (C) STRANDEDNESS: Unknown
                (D) TOPOLOGY: Linear (xi) SEQUENCE DESCRIPTION: SEQ ID NO: 13:

Asp Asp Phe
 1

(2) INFORMATION FOR SEQ ID NO: 14:

(i) SEQUENCE CHARACTERISTICS:
                (A) LENGTH: 4
                (B) TYPE: Amino Acid
                (C) STRANDEDNESS: Unknown
                (D) TOPOLOGY: Linear (xi) SEQUENCE DESCRIPTION: SEQ ID NO: 14:

Phe Asp Asp Phe
 1

( 2 ) INFORMATION FOR SEQ ID NO: 15:

( i ) SEQUENCE CHARACTERISTICS:
        ( A ) LENGTH: 2
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 15:

Asp Asp
1

( 2 ) INFORMATION FOR SEQ ID NO: 16:

( i ) SEQUENCE CHARACTERISTICS:
        ( A ) LENGTH: 2
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 16:

Asp Glu
1

( 2 ) INFORMATION FOR SEQ ID NO: 17:

( i ) SEQUENCE CHARACTERISTICS:
        ( A ) LENGTH: 2
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 17:

Asp Gln
1

( 2 ) INFORMATION FOR SEQ ID NO: 18:

( i ) SEQUENCE CHARACTERISTICS:
        ( A ) LENGTH: 8
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 18:

Phe Leu Arg Gln Asn Leu Ala Phe
1                   5

( 2 ) INFORMATION FOR SEQ ID NO: 19:

( i ) SEQUENCE CHARACTERISTICS:
        ( A ) LENGTH: 16
        ( B ) TYPE: Amino Acid
        ( C ) STRANDEDNESS: Unknown
        ( D ) TOPOLOGY: Linear     ( x i ) SEQUENCE DESCRIPTION: SEQ ID NO: 19:

Arg Gln Ala Asn Phe Leu Arg Glu Asp Leu Ala Phe Leu
1                   5                       10

Gln Gly Lys
        15

TRANSFRAME PEPTIDE INHIBITOR OF VIRAL PROTEASE

FIELD OF INVENTION

The present invention relates to the field of inhibition of viral infectivity by interrupting protease maturation and processing, as well as inhibiting of mature protease enzymatic activity.

BACKGROUND OF THE INVENTION

Inhibition of proteases is an increasingly important approach in the control of pathogenic organisms, including retroviruses. Such approaches may also be important in the preparation, processing, and maintenance of various biological materials; vaccine stability and cold-chain independent transport may be facilitated by such methods.

Retroviruses produce a polycistronic mRNA that encodes precursor molecules for the structural and functional viral proteins. A virally encoded aspartic acid protease is responsible for the processing of the polyprotein precursors Gag and Gag-Pol into the mature structural and replication enzymes. A gag-pol polyprotein homodimer forms to generate the Protease catalytic active site. Protease is then released from the precursor in an autocatalytic process. This processing is a critical step in the life cycle of retroviruses, including human immunodeficiency virus ("HIV"), the etiological agent of acquired immunodeficiency syndrome ("AIDS"). Improper processing, premature activation of the protease, or partial inhibition of the enzymatic activity during viral replication leads to defects in viral assembly and the formation of non-infectious, aberrant virus particles.

The HIV protease is autocatalytic, releasing itself from the precursor molecule by cleavage at two sites in the precursor polyprotein open reading frame ("ORF"); the amino ("N-") terminal extension of the Protease is removed, followed by cleavage at the carboxyl ("C-") terminus (Strickler et al. (1989), *Proteins* 6:139–154). Analysis of viral mutants suggested that the N- and C- cleavages are interdependent (Louis, J. M. (1991), *Euro. J. Biochem.* 199:361–369; Louis, J. M., et al. (1991), *Adv. Exp. Med. Biol.* 306:499–502). In addition, autoprocessing at the C-cleavage site is not significantly affected by the presence of the N-terminal precursor sequence. (Valverde et al. (1992), *J. Gen. Virology* 73:639–651).

A two step mechanism for autoprocessing of the HIV protease precursor polyprotein has been proposed (Louis, J. M., et al. (1994), *Proc. Natl. Acad. Sci. USA*, 91:7970–7974), wherein a first step is N-terminal Protease cleavage, releasing an active protease-polymerase intermediate(s), followed by a second step of release of mature Protease enzyme by cleavage at the C-terminus. The HIV protease autoprocessing suggests that HIV regulates protease expression in order to prevent premature complete cleavage (Arrigo, S. J., et al. (1995), *DNA and Cell Biology*, 14:15–23). It has also been noted that deletion of one region of the polyprotein precursor, the p6 region, enhances processing. (Partin, K. et al. (1991), *Proc. Natl. Acad. Sci. USA* 88(11):4776–4780).

Figure 1:
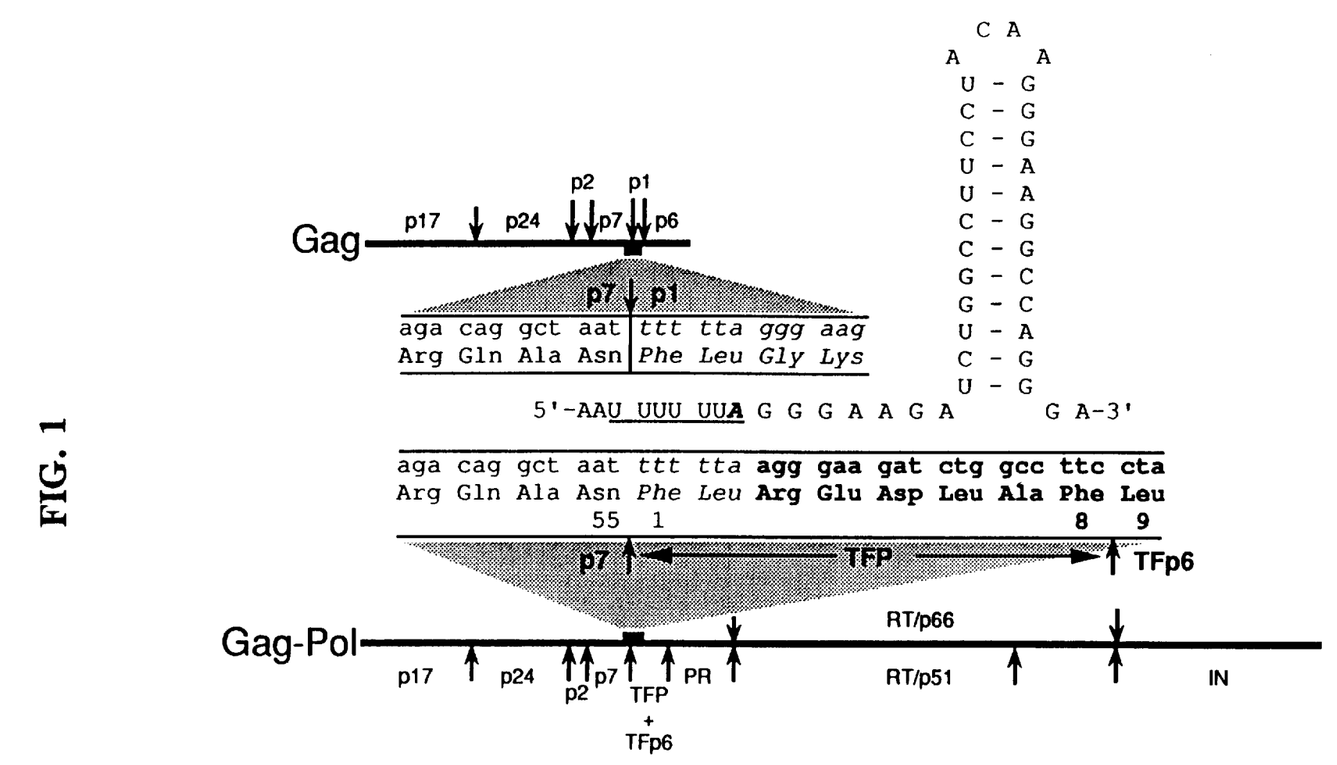

Proper processing at HIV Gag and Gag-Pol cleavage sites is crucial for viral infectivity (Robins and Plattner, (1993) *J. AIDS* 6:162–170). Cleavage sites in Gag-Pol include inter alia: p17/p24/p2/p7/p1/p6/p51/p15/p34. (See Table I, and see FIG. 1; see also Table I, *Methods in Enzymology*, 241:265, (Eds. L. C. Kuo and J. A. Shafer); Dunn, B. M., et al. (1978), *J. Biol. Chem.* 253:7269–7276).

The Gag and Gag-Pol cleavage sites are a prime target for protease inhibitors. For example, peptide-based HIV protease maturation inhibitors have been generated that target these sites in order to interfere with HIV processing (Burgess, K. and Pal, B. (1994), *Bioorganic & Med. Chem.* 2:23–26). Gag and Gag-Pol cleavage site sequences have also been modified to generate peptide-analog inhibitors (Marshall, G. R. et al., U.S. Pat. No. 5,342,922; Burgess, K. and Pal, B. (1994), *Bioorganic & Med. Chem.* 2:23–26). In addition, the p7/p6 junction of Gag has been identified as a potential target for protease inhibitors (Billich, S. et al. (1988), *J. Biol. Chem.* 263:17905–17908; Roberts, N. A., et al. (1990), *Science* 248:358–361). However, to date, very little attention has been given to the structural or functional significance of the transframe ("TF") region of the viral polyprotein.

Substrate competition is another approach for protease inhibition; target peptides corresponding to protease active site substrates compete for access to the mature enzyme recognition site. In addition, peptides and peptide analogs which mimic substrate intermediates of enzyme-catalyzed hydrolytic reactions have been described as aspartyl protease inhibitors (Rich, D. L. (1986) *Proteinase Inhibitors*, (Barrett and Salvesson, Eds.) Elsevier Science Publishers BV). Furthermore, such peptide inhibitors have been altered preventing hydrolysis of the substrate peptide bonds, thereby blocking the protease from releasing the substrate peptide and hydrolyzing the true target sequence. For example, such peptides have been used to inhibit HIV virus activity and to inhibit the proliferation of HIV in infected human lymphocytes (Voges, K. P., et al., U.S. Pat. No. 5,145,951). A limitation to this approach is that the inhibitor peptide may still be released from its complex with the protease and again become available for processing of the true target sequence.

Poor water solubility of protease inhibitors further impairs the in vivo utility of HIV peptide-based protease inhibitors (Robins, T. and Plattner, J. (1993), *J. AIDS* 6:162–170), and has been addressed by the addition of solubilizing groups such as poly-lysine, arginine methyl ester, glutamic acids, aspartic acids, Asp-Arg, Gly-Lys-Lys and dextran in order to improve the solubility of some inhibitory compounds (Toniolo, C., et al. (1994), *J. Med. Chem.* 37:4558–4562; Hostetler, K. Y., et al. (1994), *Biochem Pharmacol* 48:1399–1404). The present invention overcomes such limitations without requiring chemical modification strategies.

Thus, present day approaches cannot completely block virus activity or the resulting virus-induced pathology. Previous reports fail to identify a useful mechanism for inhibition and control of HIV protease maturation as disclosed in the present invention.

Furthermore, up to the present, no satisfactory treatment has been available which is based solely on inhibition of the mature viral protease. Current approaches to protease inhibition rely on peptides that are hydrophobic and which are directed to specific sequences of the active site in order to competitively inhibit protease activity. Such approaches are reported to result in the rapid selection of viral variants that are resistant to such inhibitors (Winslow, D. L. and Otto, M. J. (1995), *AIDS* 9 (suppl A):S183–S192).

It is therefore an object of the present invention to develop a method of inhibition of a virus encoded protease by inhibiting the maturation of the enzyme. Another object of the present invention relates to isolated forms of naturally occurring, virally encoded inhibitory peptide sequences which regulate protease maturation, arrest activation and/or reduce catalytic activity of the protease.

It is a further object of the present invention to combine competitive inhibition of protease activity with inhibition of protease maturation and therefore inhibition of activation of the protease itself. This approach will avert the rapid selection of viral variants that are resistant to the inhibitor.

Another object of the present invention relates to use the inhibitory peptides in a screening assay system of test compounds wherein additional, potent as partial protease inhibitors may be identified that also block protease activity either by competitive inhibition or by inhibition of protease maturation.

Because the natural inhibitory region is important in the control and regulation of the virus life cycle, it is a further object of the present invention to use isolated peptides derived from the inhibitory region in a formulation to stabilize a virus preparation, for example, as part of a stablilized vaccine preparation, by a method of inhibition of protease induced degradation or processing of retroviral virions. The instant TF peptide inhibitors are further packaged in the virus particle to maintain the protease and block autolysis of the protease for function early during virus infection.

Yet another object of the present invention is to use antibodies and anti-idiotypic antibodies against the inhibitor element to inhibit virion maturation and for direct treatment of virus-infected cells.

SUMMARY OF THE INVENTION

The present invention relates to an inhibitor of a crucial event in the viral life cycle, which functions by targeting maturation of a viral protease. The inhibitors of the present invention comprise an isolated portion of the transframe region of the retroviral precursor polyprotein and is referred to herein as the transframe or "TF" region. The inhibitors of the present invention are novel antiviral agents that block polyprotein maturation as well as competitively inhibiting the enzymatic activity of the mature protease. In addition, inhibition of protease maturation avoids the rapid selection of viral variant resistance mutants.

The transframe region encompasses a sequence that is released prior to the release of the fully active protease from the precursor polyprotein. It is a region wherein a reading frameshift occurs during translation of the polyprotein precursor (see FIG. 1). The inhibitors of the present invention comprise a peptide which is inhibitory of retroviral maturation and enzymatic activity. Examples of such peptides comprise SEQ ID NO: 19 and fragments thereof having protease inhibitory activity. Additional inhibitory peptides include, SEQ ID NOS: 1–18.

The scope of the present invention also relates to a method for treating HIV infections in a human comprising administering thereto an effective amount of at least one TF peptide inhibitor, or a therapeutically acceptable salt thereof.

Also included within the scope of the present invention is a method for protecting human cells against HIV pathogenesis comprising treating said cells with an anti-HIV effective amount of at least one TF peptide inhibitor compound, or a therapeutically acceptable salt thereof.

The present invention encompasses TF inhibitory peptides; pharmaceutical compositions containing the inhibitory peptides; methods of using the peptides to inhibit maturation and activity of the HIV-1 protease in treatment and prevention of HIV-induced pathogenesis; methods for screening test compounds (peptide or non-peptide) for use as HIV protease inhibitors using a complex of TF peptide inhibitor and the viral protease as a substrate; antibodies and anti-idiotype antibodies of TF peptide inhibitors; and a kit for screening compounds for use as aspartyl protease inhibitors using the peptide inhibitors and an aspartyl protease as a substrate.

The present invention is the first disclosure of TF peptides as inhibitors of protease maturation and of protease enzyme activity. The peptides described by the present invention are short and highly water soluble.

According to the present invention, the TF peptide inhibitor comprises a peptide with about 2 to 20 amino acids arranged in a specific sequence which is useful for the inhibition of HIV protease by blocking maturation of the protease and by competitive inhibition of the enzymatic activity of the mature protease.

BRIEF DESCRIPTION OF THE DRAWING

FIG. 1. Sequence surrounding the frame-shift site in HIV-1: The Gag and Pol polyproteins of HIV-1 are indicated by bolded lines. Short arrows indicate the various sites of cleavage by the viral protease. The DNA and protein sequences spanning transframe cleavage junctions in the Gag-Pol polyprotein are shown. The RNA sequence spanning the conserved signal sequence 6UA (underlined) and the secondary structure is shown. TFP and TFp6 denote the eight TF peptide residues flanking the Gag p7 (Phe1 to Phe8) and remainder of the transframe region residues Phe9 to the N-terminus of the protease, respectively. The DNA and corresponding protein sequence of the Pol open reading frame are shown in bolded letters. Gag p1 amino acids are italicized.

FIG. 2. Lineweaver-Burk plots of HIV-1 protease catalyzed hydrolysis of substrate 1 at various concentrations of the inhibitor tripeptide, Glu-Asp-Leu referred to herein as "EDL" in 50 mM sodium formate at pH 4.25 containing 150 mM of HIV-1 protease, 2.5 mM dithiothreotol ("DTT") at 25° C. Inset is a plot of the apparent $K_m$ versus inhibitor concentration.

FIG. 3. A plot of $K_i$ for HIV-1 protease-catalyzed hydrolysis of substrate 1 vs. pH. $K_i$ was obtained from a plot of 1/V versus inhibitor concentration (referred to herein as "[I]") at a saturating concentration of substrate 1 (390 $\mu$M). Reactions were carried out between pH values of 3 to 5 in 50 mM sodium formate or 100 mM sodium acetate buffers containing 150 mM of HIV-1 protease, 2.5 mM DTT at 25° C.

DETAILED DESCRIPTION OF THE INVENTION

The present invention relates to the identification of a transframe ("TF") region within a retroviral polyprotein containing a novel TF peptide inhibitor of retroviral protease. This inhibitor appears to play a regulatory role in the retroviral life-cycle by modulating the synthesis of active retroviral protease. The TF peptide inhibitors of the present invention function as inhibitors of retroviral protease maturation. In addition, the TF peptide inhibitors act as competitive inhibitors of enzymatic activity of the functional, mature viral protease.

The TF peptide inhibitors of the present invention may be functional in many retroviral systems to curb the spread of infective virus. In particular, the spread of human immunodeficiency viruses (known as "HIV") such as HIV-1 and HIV-2 may be inhibited by a TF peptide inhibitor. Other retroviruses which may be inhibited by the TF peptide inhibitors of the present invention include, but are not limited to, HLV-I, HTLV-II, BLV, EIAV, FIV, SIV, STLV and Visna virus. The TF peptide inhibitors of the present invention also inhibit other mammalian aspartyl proteases.

The TF peptide inhibitor region of the present invention comprises the transframe region, located within the Gag-Pol polyprotein precursor. In particular, the "transframe" or "TF region" encompasses a region wherein a translational frameshift occurs. TF peptide inhibitor sequences exist within this region and comprise a highly conserved sequence. One preferred TF region encompasses a short region of p7, and four amino acids at either end flanking the N- and C- termini of TFP6 and p7 respectively (see FIG. 1, and Table 1). Another preferred region comprises SEQ ID NO: 19 or fragments thereof, wherein the fragments have aspartyl protease inhibitory activity. "Fragments", as the term is used herein comprises sequences which are shorter than the named sequence and have the characteristics of being inhibitory of aspartyl protease activity. Fragments of a particular sequence can vary in length and in fact, may be as short as 2 amino acids in length. Fragments may further carry modified amino acids, peptide bonds or end groups.

A "peptide," as the term is used herein, is a sequence of amino acids linked together in a chain by peptide bonds. The term "peptide" includes peptide analogs, wherein one or more amino acid side chains, reactive groups, peptide bonds, or other moieties have been altered either through chemical modifications or by some other process. In producing the TF peptide inhibitors of the present invention, it may be desirable to modify the peptides, the amino acids or the peptide linkages in one or more positions of the peptide sequence. For example, it may be advantageous to alter the peptide bond to render it non-hydrolyzable. It will be understood by those skilled in the art that such modifications may be achieved by standard procedures (Winslow, D. L. and Otto, M. J. (1995), *AIDS* 9 (suppl A):S183–S192; Meek, T. D. (1992), *J. Enzym. Inhib.* 6:65–98; Vaillancourt, M.. et al. (1994) *Bioorg. Med. Chem.,* 2:343–355). It will further be understood by those skilled in the art that other modifications capable of blocking protease cleavage can be used to achieve inhibition.

The term "pharmaceutically acceptable carrier" as used herein means a non-toxic, generally inert vehicle for the active ingredient, which does not adversely affect the ingredient.

The term "effective amount" as used herein means a predetermined amount of the peptides of this invention sufficient to be effective against a retroviral infection, such as HIV in a human. An effective amount may also refer to an amount sufficient to inhibit aspartyl protease activity.

In addition to inhibiting the enzymatic activity of the protease, the TF peptide inhibitors of the present invention play a regulatory role in the HIV lifecycle. During the HIV lifecycle, two HIV polyprotein precursors, Gag and Gag-Pol are cleaved by the HIV-encoded protease to yield mature viral structural and functional proteins, including the protease itself. The mature protease exhibits 300–600 fold greater proteolytic activity than precursor protease contained within the Gag-Pol precursor. Even partial inhibition of protease activity interferes with the HIV lifecycle and leads to defects in viral assembly including the production of non-infectious virion particles. The Gag-Pol precursor polyprotein containing both the TF peptide inhibitor region and a protease regulates the HIV lifecycle by maintaining the protease in a relatively inactive form with low enzymatic activity at neutral pH, called cis regulation, until the polyproteins are assembled into immature particles. At that point, reduction of pH (optimal at pH 5.0) results in cleavage and excision of the TF inhibitor from the precursor polyprotein. The mature, fully active protease is then released from the polyprotein by a subsequent intramolecular cleavage at its N-terminus and a intermolecular cleavage at its C-terminus. This mature protease then hydrolyses other cleavage site peptide bonds in the Gag and Pol domains to release the necessary mature enzymes and structural proteins for virus maturation, unless a TF inhibitor is present, in which case protease enzymatic activity is inhibited in trans.

Additionally, a TF peptide inhibitor of the present invention also may trap and maintain the protease in an inactive form in the cores of the infective virions, in cis or trans, thereby blocking autolysis.

The inhibitory activity of the TF peptides is pH dependent. For example, inhibition of the HIV protease by TF peptide inhibitors is optimal between pH 3–7 (see FIG. 3).

In one embodiment of the present invention, the TF peptide inhibitor comprises a 16 amino acid peptide, "RQANFLREDLAFLQGK" (SEQ ID NO: 19) encoded within the N-terminal amino acid segment of the transframe region of HIV-1, or fragments of SEQ ID NO: 19 which have aspartyl protease inhibitory activity.

In another embodiment of the present invention the TF peptide inhibitor comprises a specific eight amino acid peptide, "FLREDLAF" (SEQ ID NO: 1) encoded within the N-terminal amino acid segment of the transframe region of HIV-1.

In yet another embodiment of the present invention a specific three amino acid peptide, EDL (SEQ ID NO: 4) provides potent inhibitory activity. The EDL peptide strongly and selectively inhibits the HIV aspartic acid protease, as demonstrated by its inability to inhibit pepsin, a mammalian aspartic acid protease. Further, the EDL peptide is highly soluble in water, in contrast to previously described peptide inhibitors. In addition, binding of a TF peptide inhibitor to the HIV protease is not dependent on a high salt concentration.

Smaller TF peptide inhibitor compositions include, but are not limited to FLREDLAF (SEQ ID NO 1), GEDLAF (SEQ ID NO 2), EDLA (SEQ ID NO 3), EDL (SEQ ID NO 4), RED (SEQ ID NO 5), DLAF (SEQ ID NO 6), DEL (SEQ ID NO 7), EEL (SEQ ID NO 8), DDL (SEQ ID NO 9), ENL (SEQ ID NO 10), EKF (SEQ ID NO 11), EDF (SEQ ID NO 12), DD (SEQ ID NO 15), DE (SEQ ID NO 16), DQ (SEQ ID NO 17), DDF (SEQ ID NO 13), or FDDF (SEQ ID NO 14). (See Table 2). For example, the three amino acid peptide, EDL ("the trimer") is a short, water soluble peptide with highly potent protease inhibitory character.

The TF peptide inhibitor can be synthesized in a number of ways. The peptides can be isolated from viral source material. The peptides may also be chemically synthesized, free of any HIV virus, reducing risk of exposure to virus to zero. Chemical synthesis ensures a high degree of homogeneity under controlled conditions and permits chemical modifications to be incorporated along the way (Merrifield, R. B. (1963), *J. Amer. Soc.,* 85:2149).

Alternatively, the peptides may be produced by recombinant DNA techniques using methods such as those in Sambrook, 1988, *Molecular Cloning: A Laboratory Manual* (2nd Edition) that are well understood in the art.

The TF peptide inhibitors may be modified by techniques understood in the art (Winslow, D. L. and Otto, M. J. (1995), *AIDS* 9 (suppl A) :S183–S192; Meek, T. D. (1992), *J. Enzym. Inhib.* 6: 65–98; Rich, D. L. (1986), *Proteinase inhibitors,* (Barrett and Salvessen, Eds.) Elsevier Science Publications, BV), substituting one or more amino acid side-chain groups or other groups or bonds or linkages in order to improve the inhibitory character of the peptide. For example, alteration of the peptide bond in order to render the peptide non-hydrolyzable, by the "NOR" method described by Burgess, K. and Pal, B. ((1994), *Bioorganic & Med. Chem.* 2:23–26) in which the "Nor" peptide analog inhibitors exclude the natural cleavage/active sites. Other modifications may include aldehydes (Sarubbi, E., et al. (1993) *FEBS Lett.,* 319:253–256) or "Mirror" D-amino acids which act as irreversible inhibitors blocking hydrolysis. The maintenance of the three dimensional conformation, physical constraints or molecular interactions may preserve the inhibitory quality of the TF peptide inhibitors found in the virion. Furthermore, the TF peptide inhibitors can be used to obtain crystallographic information regarding the three dimensional structure of the TF peptides alone or complexed with the protease. This information may suggest new inhibitors through molecular modelling techniques as known in the art.

The ability of TF peptides to inhibit aspartyl proteases, such as HIV aspartyl protease is significant. Use of such peptides in a pharmaceutical composition allows for the control and regulation of HIV protease in vitro and in humans infected with the HIV virus. TF peptide inhibitors can therefore be used to control and regulate HIV virus activity in vitro and in vivo. It is recognized that inhibition of the HIV protease has important implications for control of HIV infection in humans.

In one preferred embodiment, the TF peptides are used to inhibit HIV activity in a population of cells. For example, the TF peptide inhibitor may be used to inhibit virus activity in a retrovirally infected human. One or more peptides may be used to treat, for example, an HIV infected patient.

The peptides of this invention can be obtained in the form of a therapeutically acceptable salt. In the instance where a particular peptide has a residue which functions as a base, examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrothalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by Boissonnas, R. A., et al. ((1960), *Helv. Chim. Acta,* 43:1849).

In the instance where a particular peptide has one or more free carboxyl groups, examples of such salts are those with the sodium, potassium or calcium cations, or with strong organic bases, for example, triethylamine or N-methylmorpholine.

In general, the therapeutically acceptable salts of the peptides are biologically fully equivalent to the peptides themselves.

The cell protective effect of the peptides or their therapeutically acceptable salts can be demonstrated by microbiological procedures for evaluating the effect of test compounds in inhibiting the cytopathogenicity of HIV in human $CD4^+$ cell types; for example, see Baba, M., et al. ((1987), *Biochem. Biophys, Res. Comm.,* 142:128).

When peptides of the instant invention, or a therapeutically acceptable salt thereof, is used to combat HIV infections in a human, such peptides can be administered orally, topically or parenterally, in a vehicle comprising one or more pharmaceutically acceptable carriers, the proportion of which is determined by the solubility and chemical nature of the peptide, chosen route of administration and standard biological practice. For oral administration, the peptides or a therapeutically acceptable salt thereof can be formulated in unit dosage forms such as capsules or tablets each containing a predetermined amount of the active ingredient, ranging from about 25 to 500 mg, in a pharmaceutically acceptable carrier. For topical administration, the peptides can be formulated in a pharmaceutically acceptable vehicle containing 0.1 to 10 percent, preferably 0.5 to 5 percent, of the active agent. Such formulations can be in the form of a cream, lotion, sublingual tablet, or preferably a transdermal patch or buccal patch.

The pharmaceutical composition of the present invention can take the form of a lyophilized powder of the active substance, to be dissolved immediately before use in a physiological solution for the purpose of injection. For parenteral administration, the peptide of the formula is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantities of pharmaceutically acceptable salts or of glucose to make the solution isotonic. The pharmaceutical composition according to the invention can also take a form which is suitable for oral administration. For example, suitable forms are tablets, food gelatin capsules, dragées, powders and granules. The formation of such oral forms is well-known to those skilled in the art. Any of the known formulations are useful in preparing the instant oral pharmaceutical compositions.

The present invention also covers the use of TF peptide inhibitor compositions in combination with other medicinal compositions intended for the treatment of retroviral infections and tumors. Immunostimulants and immunomodulators such as for example cytokines, including IL-2, IL-12 and interferon molecules can be used in combination with the present invention.

Suitable vehicles or carriers for the above noted formulations can be found in standard pharmaceutical texts, e.g. in "Remington's Pharmaceutical Sciences", 16th ed. Mack Publishing Company, Easton, Pa., 1980.

The dosage of the peptide will vary with the form of administration, the frequency of administration, the nature and severity of the infection and the particular active peptide agent chosen. Furthermore, it will vary with the particular host under treatment. Generally, treatment is initiated with small dosages substantially less than the optimum dose of the peptide. Thereafter, the dosage is increased by small increments until the optimum effect under the circumstances is reached. The actual dosage administered will be determined by physiological factors such as age, body weight, severity of condition and/or chemical history of the patent. With these considerations in mind, the dosage of the TF peptide inhibitor composition for a particular subject can be readily determined by the physician. In general, the peptide is most desirably administered at a concentration level that will generally afford antivirally effective results without causing harmful or deleterious side effects. However, it is noted that in extreme cases a dosage approaching the toxic level may be an acceptable treatment protocol.

For oral administration, the peptide or a therapeutically acceptable salt is administered in the range of 0.01 to 75 mg per kilogram of body weight per day, with a preferred range of 2.5 to 20 mg per kilogram.

With reference to systemic administration, the peptide of the formula is administered at a dosage of 10 µg to 1000 mg per kilogram of body weight per day, although the aforementioned variations will occur. However, a dosage level that is in the range of from about 50 µg to 500 mg per kilogram of body weight per day is most desirably employed in order to achieve effective results.

Although the formulations disclosed hereinabove are effective and relatively safe medications for treating HIV infections, the possible concurrent administration of these formulations with other antiviral medications or agents to obtain beneficial results is not excluded. Such other antiviral medications or agents include soluble CD4, thalidomide, dideoxyinosine, dideoxythymine, zidovudine, dideoxycytidine, gancyclovir, acyclovir, phosphonoformate, amatradine, ribavarin, antiviral interferons (e.g. α-interferon, α-interferon, or interleukin-2) or aerosol pentamidine, and other substances used in anti-HIV therapy in particular, the TF peptide inhibitor formulations may be used in conjunction with other protease inhibitors such as those described in Winslow, D. L. and Otto, M. J. ((1995), *AIDS* 9 (supp A):S183–S192).

Treatment of infected cells to inhibit virus activity may be for a specific period of time or may be continuous. Virus activity may be measured by monitoring levels of viral protein, such as P24, or by measuring reverse transcriptase levels, or by monitoring virus protein activity by $^{35}$S-met pulse-chase labelling and immunoprecipitation experiments, or by other methods which are well known by one of skill in the art. (Kayeyama, S., et al. (1994), *AIDS Res. and Human Retroviruses*, 10:735–745).

Another embodiment of the present invention relates to the generation and use of antibodies directed against the TF peptide inhibitors. Such antibodies have many uses. The anti-TF peptide inhibitor antibodies can be used to inhibit virus activity directly by binding to the TF peptide inhibitor sequence, thereby blocking cleavage and release of the mature protease. Also, the anti-TF peptide inhibitor antibodies can be used to generate anti-idiotypic antibodies that can directly interfere with protease activity itself. Anti-TF peptide inhibitor antibodies and any anti-idiotypic antibodies, may be used as "intracellular vaccines" in treating virally infected cells. Such intracellular uses involve the use of so-called single chain antibodies which can be introduced into cells by methods well-known in the art (Huston, J. S., et al. (1988), *Proc. Natl. Acad. Sci., USA*) or may be directly expressed within cells under the appropriate cellular controls.

The present invention further relates to antibodies and anti-idiotype antibodies generated from TF peptide inhibitor, (also referred to as "TF antibodies"). In this embodiment of the invention, TF antibodies are monoclonal or polyclonal in origin. The TF peptide inhibitors used to generate the TF antibodies may be from natural or recombinant sources or generated by chemical synthesis. Natural TF inhibitor peptides can be isolated from viral samples. Synthetic TF inhibitor peptides may be custom ordered or commercially made based on the amino acid sequences of the present invention or chemically synthesized by methods known to one skilled in the art (Merrifield, R. B. (1963), *J. Amer. Soc.,* 85:2149). If the peptide is too short to be antigenic it may be conjugated to a carrier molecule to enhance the antigenicity of the peptide. Examples of carrier molecules, include, but are not limited to, human albumin, bovine albumin and keyhole limpet hemo-cyanin ("Basic and Clinical Immunology" (1991) Stites, D. P. and Terr A. I. (eds) Appleton and Lange, Norwalk, Conn., San Mateo, Calif.).

Exemplary antibody molecules for use in the detection methods of the present invention are intact immunoglobulin molecules, substantially intact immunoglobulin molecules or those portions of an immunoglobulin molecule that contain the antigen binding site, including those portions of immunoglobulin molecules known in the art as F(ab), F(ab'), $F(ab')_2$ and F(v). Polyclonal or monoclonal antibodies may be produced by methods known in the art (Kohler and Milstein (1975), *Nature* 256:495–497; Campbell (1985), *Laboratory Techniques in Biochemistry and Molecular Biology,* Vol. 13, Burdon, et al. (Eds.), Elsevier Science Publishers, Amsterdam). The antibodies or antigen binding fragments may also be produced by genetic engineering. The technology for expression of both heavy and light chain genes in *E. coli* is the subject of the PCT patent applications: publication number WO 901443, WO 901443, and WO 9014424 and in Huse et al. (1989), *Science* 246:1275–1281.

The present invention is particularly advantageous in the control of virus infection in that the TF peptide inhibitors combine inhibition of protease maturation with a powerful competitive inhibitory activity against mature protease. Indeed, this two-fold activity is a substantial advance. With the TF peptides inhibitors of the present invention, mature protease production is dramatically reduced, and any available mature or nascent protease is secondarily inhibited by a competitive mechanism.

Yet another embodiment of the present invention relates to use of the peptides to identify new compounds, such as peptides or non-peptides with even greater anti-viral properties for inhibiting protease activity and/or maturation in a screening assay. A test screening kit, relying on the well-understood methods of competitive inhibition has been developed based on the TF peptides. Such a kit comprises a protease and at least one TF peptide inhibitor, which forms a complex, said complex or protease being bound to a solid support, such as a magnetic bead or plastic matrix. In some cases, it may be preferred that the peptide(s) are labelled. Labelling agents are well-known in the art. For example, labelling agents include but are not limited to radioactivity, chemiluminescence, bioluminescence, luminescence, or other identifying "tags" for convenient analysis.

Varying amounts of test compounds, such as peptides or non-peptide compounds are added to the complex in order to displace of the original peptide complexes. Analysis of the release of the peptides, by, for example, monitoring the identifying tag or label following incubation with the test sample, indicates the relative binding affinity of the test sample in the complex and thus is indicative of identification of a new anti-viral compound. The new complex may then be assayed for inhibition of protease activity by standard kinetic assays (see Example 2 below; Ferhst, A. (1977), *Enzyme Structure and Mechanisms,* W. H. Freeman and Co., San Francisco; Segal, I. H. (1975), *Enzyme Kinetics,* John Wiley and Sons, New York).

Solid matrices are available to the skilled artisan. Solid phases useful as matrices for the present invention include but are not limited to polystyrene, polyethylene, polypropylene, polycarbonate, or any solid plastic material in the shape of test tubes, beads, microparticles, dip-sticks, plates or the like. Additionally matrices include, but are not limited to membranes, 96-well microtiter plates, test tubes and Eppendorf tubes. Solid phases also include glass beads, glass test tubes and any other appropriate shape made of glass. A functionalized solid phase such as plastic or glass which has been modified so that the surface carries carboxyl, amino, hydrazide, or aldehyde groups can also be used. In general such matrices comprise any surface wherein a ligand-binding agent can be attached or a surface which itself provides a ligand attachment site.

The test compound may be any peptide or non-peptide composition in a purified or non-purified form. Chemical compounds, synthetic compounds, biological compounds or other specimens may be used from any source, including plant and animal. The test compound may also comprise a complex mixture or "cocktail" of molecules.

Figure 3:
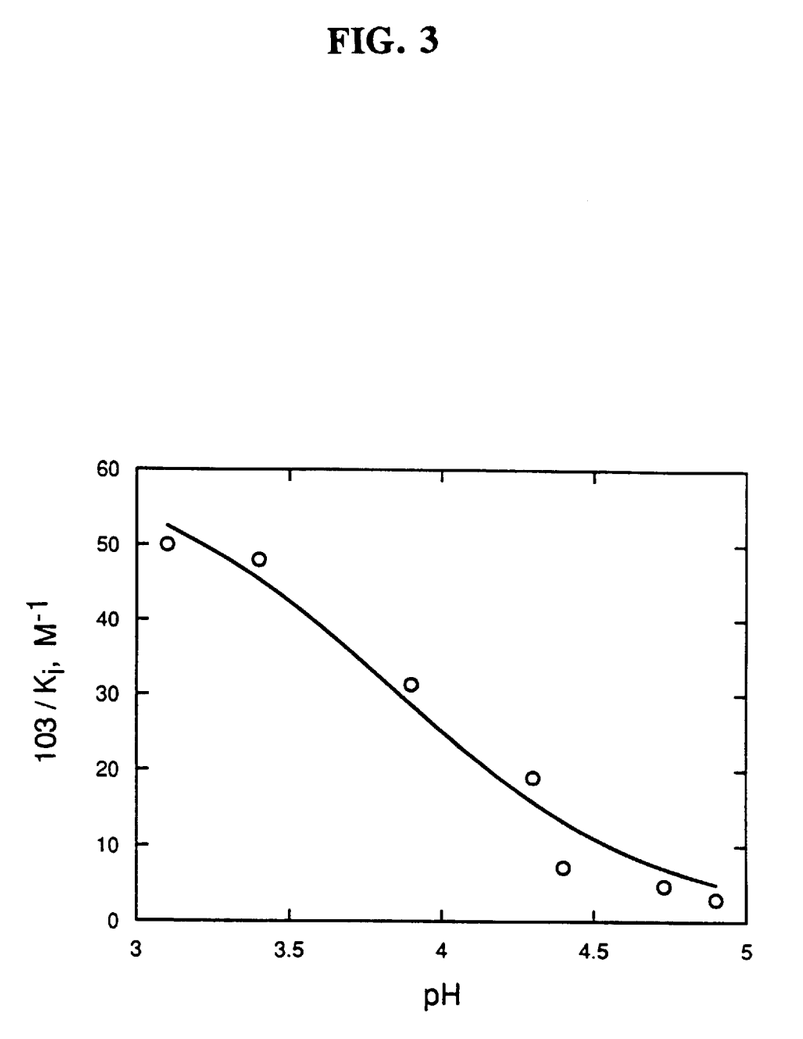

Another embodiment of the present invention involves a method for stabilizing virus preparations. Virus degradation is delayed at low temperatures and vaccine preparations often require storage at low temperature (below 0° C.). Treatment of virus preparations, such as virus-based vaccine preparations with the TF peptide inhibitors of the present invention serves to reduce or even obviate the need for cold storage of virus or vaccine preparations, by inhibiting the proteolytic activity of the protease contained in the viral preparation.

pH-rate profile for the autoprocessing reaction showed that cleavage of the N-terminal TFp6 to release the mature Protease is dependent on the ionization of groups with $pK_a$'s of 4.9 and 5.1 (see FIG. 3).

Autoprocessing of ΔTFP-TFp6-PR precursor to produce the mature Protease occurs in two steps. In the first step, the Protease hydrolyses the peptide bond corresponding to the ΔTFP-TFp6 junction to produce the enzyme intermediate, TFp6-PR. The TFp6-PR which possesses low intrinsic catalytic activity, comparable to that of Δ TFP-TFp6-PR is then converted in a second step to the mature Protease concomitant with a large increase in enzymatic activity.

Table 1 sets forth the cleavage recognition sequences for HIV-1 polyprotein cleavage sites. In addition, Table 1 demonstrates the relative efficiency of cleavage at each site, based upon $K_{cat}/K_m$.

TABLE 1

| Gag Cleavage Sites | | $k_{cat}/K_m$, mM$^{-1}$s$^{-1}$ | Pol Cleavage Sites | | $k_{cat}/K_m$, mM$^{-1}$s$^{-1}$ |
|---|---|---|---|---|---|
| p17/p24 | SQNY*PIVQ | 45.0 | p7/TFP | ERQAN*FLRED | 1.9 × 10$^{-5}$ |
| p24/p2 | ARVL*AEAM | 90.0 | TFP/TFp6 | DLAF*LQGK | 1.2 |
| p2/p7 | ATIM*MQRG | 74.0 | TFp6/PR* | SFNF*PQIT | 7.0 |
| p7/p1 | RQAN*FLGK | 1.6 | PR/RT | TLNF*PISP | 24.0 |
| p1/p6 | PGNF*LQSR | 0.6 | RT/RN | AETF*YVDG | 10.0 |
| | | | RN/IN | RKIL*FLDG | 200.0 |

*PR refers to HIV-1 protease.

For example, a live, attenuated virus-based vaccine, a killed virus vaccine, or a sub-unit vaccine preparation may be stabilized in the presence of the protease inhibitors described by the present invention. Furthermore, polyprotein or protease preparations may be similarly treated and stabilized.

All publications, patents and articles referred to herein are expressly incorporated herein in toto by reference thereto. The following examples are presented to illustrate the present invention but are in no way to be construed as limitations on the scope of the invention. It will be recognized by those skilled in the art that numerous changes and substitutions may be made without departing from the spirit and purview of the invention.

EXAMPLE 1

REGULATION OF PROTEASE MATURATION AND AUTOPROCESSING

HIV protease ("PR") was fused to 48 amino acids of the native transframe sequence ("TFp6") at its N-terminus, designated TFp6-PR. In another protease fusion, ΔTFp6-TFp6-PR, 6 amino acids of the transframe octapeptide (SEQ ID NO: 1) (ΔTFP; Δ=truncated) further flanking the TFp6 were fused to TFp6-PR. The first-order rate constant for the autoprocessing of TFp6-PR to release the mature Protease is identical to previously published results for the autoprocessing of the model precursor MBP-ΔTF-PR-ΔPol providing direct evidence that the intramolecular cleavage that occurs at the N-terminus of Protease is independent of the length of sequence flanking the terminus of the Protease. The rate of disappearance of TFp6-PR and that of the appearance of the mature Protease and enzymatic activity are identical. The first order rate constant is identical to that reported for the model polyprotein, MBP-ΔTF-PR-ΔPol (Louis, J. M., et al. (1994), *Proc. Nat'l. Acad. Sci. USA*, 91:7970–7974). The

EXAMPLE 2

INHIBITION OF HIV-1 PROTEASE BY TF PEPTIDE INHIBITORS

Peptides were at least 98% pure as determined by chromatography. Stock solutions of all peptides were prepared in water except peptides 1 and 2 (see Table 2) which were dissolved in 50 mM sodium bicarbonate. The solution concentration of peptides containing phenylalanine was determined spectrophotometrically at 257 nm using the extinction coefficient for acetylphenylalanine in water as described in *CRC Handbook of Biochemistry*, Ed. H. A. Sober, The Chemical Rubber Co., Cleveland Ohio.

HIV-1 protease was obtained and its active site concentration was determined at 25° C. Purified enzyme was stored as a 5–8 μM stock solution in 50 mM NaOAc (pH 5.0), 1 mM DTT, 1 mM EDTA, 0.05% reduced Triton X-100 at −80° C. Porcine pepsin was prepared as 1–2 mg/ml in 50 mM formic acid (pH 3.0). The peptide concentrations were adjusted for their protein content.

HIV-1 protease activity was measured at 25° C. using substrate I (Lys-Ala-Arg-Val-Nle-Phe (NO$_2$) -Glu-Ala-Nle-NH$_2$ wherein Nle is norleucine and Phe (NO$_2$) is 4-nitrophenylalamine). In a typical assay, 2.5 μl of enzyme was added to 97.5 μl of buffer and 2.5 mM DTT in the presence or absence of varying concentrations of inhibitor. The reaction was initiated by the addition of 10 μl of a 4 mM solution of substrate I in water and monitored by following the decrease in absorption at 310 mM in a 100 μl spectrophotometric cell. Pepsin was assayed using substrate II (Phe-Gly-His-Phe(NO$_2$)-Phe-Ala-PheOCH$_3$). The reaction was monitored by following the decrease in absorbance at 269 nm in a final volume of 110 μl of 50 mM formate buffer, pH 3.0, containing 150 mM and 160 μM enzyme and substrate, respectively, at 25° C. Concentrations of substrate solutions were determined spectrophotometrically at 280 mm.

Figure 2:
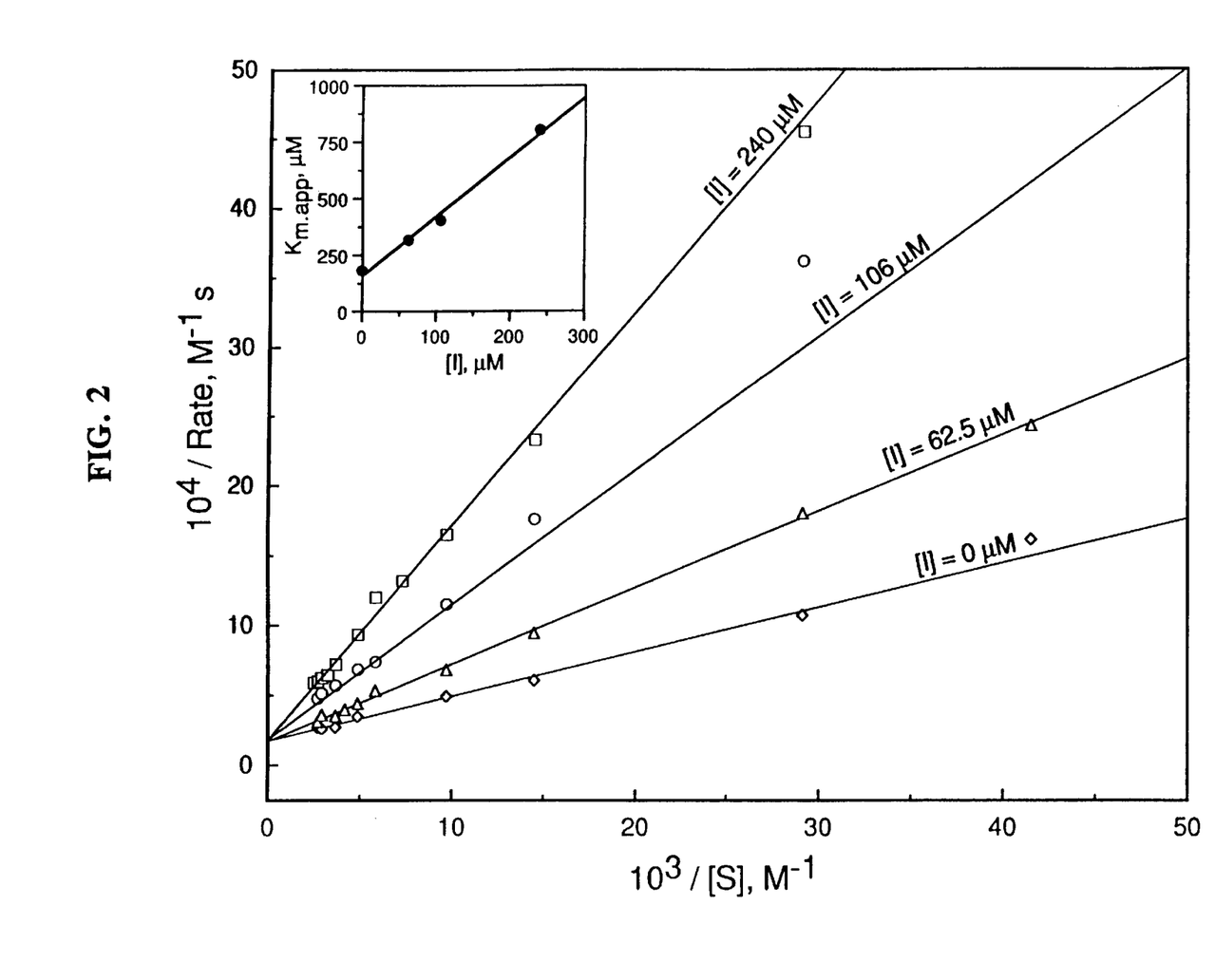

$K_i$ was obtained from a plot of the apparent $K_m$ vs. [I] for peptides 1 (SEQ ID NO: 1), 2 (SEQ ID NO: 2), and 4 (SEQ ID NO: 4) as shown in FIG. 2. For the others, $K_i$ was obtained from a plot of 1/V vs [I] at a saturating concentration of the substrate. The enzyme was assayed in the presence of the inhibitor in 50 mM sodium formate at pH 4.25 and 2.5 mM DTT. The final enzyme and substrate concentrations were 150 mM and 390 μM, respectively. Peptides 12a and 12b were assayed at pH 4.4 and contained 0.083% and 0.02% DMSO, respectively. ND indicates no inhibition tested up to a concentration of 50 mM peptide.

The octapeptide (SEQ ID NO: 1) and shorter peptides are competitive inhibitors for HIV-1 protease-catalyzed hydrolysis of substrate I as shown in FIG. 2. The measured $K_i$'s are provide in Table 2.

ID NO: 6) to the enzyme. As shown in Table 3, the $K_i$ for the peptide, Glu-Asp-Leu, inhibition of HIV-1 protease-catalyzed hydrolysis of substrate I was 435±65 μM and 1001±170 μM in the presence of 1M and 2M NaCl, respectively (50 mM sodium formate, pH 4.0, and 2.5 mM DTT at 25° C.). Similarly, the $K_i$ for Glu-Asp-Phe and the tetrapeptide, Asp-Leu-Ala-Phe increased to 410±25 μM and 3260±390 μM, respectively, in the presence of 1M NaCl.

TABLE 3

| PEPTIDE | NaCl Concentration, M | $K_i$ M |
|---|---|---|
| Glu—Asp—Leu | 0 | 52 ± 10 |
| (SEQ ID NO: 4) | 1 | 435 ± 65 |

TABLE 2

| | PEPTIDE | | $K_i$, μM |
|---|---|---|---|
| 1 | Phe—Leu—Arg—Glu—Asp—Leu—Ala—Phe | (SEQ ID NO: 1) | 98 ± 10 |
| 2 | Gly—Glu—Asp—Leu—Ala—Phe | (SEQ ID NO: 2) | 64 ± 13 |
| 3 | Glu—Asp—Leu—Ala | (SEQ ID NO: 3) | 160 ± 20 |
| 4 | Glu—Asp—Leu | (SEQ ID NO: 4) | 50 ± 9 |
| 5 | Arg—Glu—Asp | (SEQ ID NO: 5) | 3360 ± 400 |
| 6 | Asp—Leu—Ala—Phe | (SEQ ID NO: 6) | 270 ± 25 |
| 7 | Asp—Glu—Leu | (SEQ ID NO: 7) | 230 ± 20 |
| 8 | Glu—Glu—Leu | (SEQ ID NO: 8) | 310 ± 25 |
| 9 | Asp—Asp—Leu | (SEQ ID NO: 9) | 140 ± 6 |
| 10 | Glu—Asn—Leu | (SEQ ID NO: 10) | 3070 ± 210 |
| 11 | Glu—Lys—Phe | (SEQ ID NO: 11) | 2010 ± 360 |
| 12 | Glu—Asp—Phe | (SEQ ID NO: 12) | 25 ± 3 |
| 12 a | Asp—Asp—Phe | (SEQ ID NO: 13) | 43 ± 7 |
| 12 b | Phe—Asp—Asp—Phe | (SEQ ID NO: 14) | 55 ± 14 |
| 13 | Asp—Asp | (SEQ ID NO: 15) | 970 ± 140 |
| 14 | Asp—Glu | (SEQ ID NO: 16) | 5400 ± 380 |
| 15 | Asp—Gln | (SEQ ID NO: 17) | >1000 |
| 16 | Glutamic acid | | ND |
| 17 | Aspartic acid | | ND |
| 18 | Phe—Leu—Arg—Gln—Asn—Leu—Ala—Phe | (SEQ ID NO: 18) | 2000 |

Table 2. $K_i$ was obtained from a plot of the apparent $K_m$ vs. [I] for peptides 1, 2 and 4 as shown in FIG. 2. For the others, $K_i$ was obtained from a plot of 1/V vs [I] at a saturating concentration of the substrate. The enzyme was assayed in the presence of the inhibitor in 50 mM sodium formate at pH 4.25 and 2.5 mM DTT. The final enzyme and substrate concentrations were 150 mM and 390 μM, respectively. Peptides 12a and 12b were assayed at pH 4.4 and contained 0.083% and 0.02% dimethyl sulfoxide ("DMSO"), respectively. "ND" indicates no inhibition tested up to a concentration of 50 mM peptide. EDL has the smallest $K_i$ which is similar to the hexapeptide (peptide 2) and its analog EDF (peptide 12).

The rate of HIV-1 protease-catalyzed hydrolysis of substrate I measured upon initiating the reaction by addition of the enzyme to inhibitor/substrate I mixture was equal to the rate in which the reaction was initiated by the addition of substrate I to a pre-incubated mixture (10 min) of enzyme and inhibitor. Thus, the binding of these inhibitors was rapid and reached equilibrium with the enzyme in less than 15 seconds.

EXAMPLE 3

CHARACTERISTICS OF TF INHIBITORS

Binding TF peptide inhibitors to the enzyme is dependent on an ionizable group in its protonated form with a $pK_a$ of 3.8 (FIG. 3). The pH rate profile for HIV protease-catalyzed hydrolysis of peptide substrates showed $pK_a$ values of 3.4–3.7 for the basic group and 5.5 to 6.5 for the acidic group. The observed pH dependence suggested that the tripeptide inhibitor, EDL (SEQ ID NO: 4) interacts with the catalytic aspartic acid residue at the active site. Increasing NaCl concentration decreased the affinity of the inhibitors Glu-Asp-Leu (SEQ ID NO: 4) and Asp-Leu-Ala-Phe (SEQ TABLE 3-continued

| PEPTIDE | NaCl Concentration, M | $K_i$ M |
|---|---|---|
| | 2 | 1001 ± 170 |
| Glu—Asp—Phe | 0 | 15 ± 2 |
| (SEQ ID NO: 12) | 1 | 410 ± 25 |
| Asp—Leu—Ala—Phe | 0 | 270 ± 25 |
| (SEQ ID NO: 6) | 1 | 3260 ± 390 |

Table 3. $K_i$ was obtained from a plot of 1/V vs [I] at saturating concentration of the substrate. The enzyme was assayed in the presence of the inhibitor in 50 mM sodium formate at pH 4.25 and 2.5 mM DTT. The final enzyme and substrate concentration were 150 mM and 390 μM respectively.

These results indicated that the interactions between the enzyme and inhibitor appear to be mostly hydrophilic in nature, i.e., electrostatic and hydrogen bonding, even in the presence of the one hydrophobic residue is the case in peptide 12, Glu-Asp-Phe (SEQ ID NO: 12). The results also indicate that the observed increase in $K_i$ at 0M NaCl for the tripeptide analog, Glu-Asp-Phe (SEQ ID NO: 12), is not due an increase in the hydrophobic affinity to bind to the active site cavity of the enzyme as a result of the substitution of a Phe in the place of Leu at the C-terminus.

EXAMPLE 4

GLU-ASP-LEU (SEQ ID NO: 4) IS A COMPETITIVE INHIBITOR FOR THE MAMMALIAN ASPARTIC ACID PROTEASE, PEPSIN

Using the procedures described in Example 2, the $K_i$ value for the inhibition of pepsin by Glu-Asp-Leu (SEQ ID NO: 4) was found to be about 150 fold higher (7.5 mM at pH 3.0) than that for the inhibition of HIV protease. Thus, HIV protease was more selectively inhibited by EDL and its analogs in the presence of other mammalian proteases. Such selective inhibition facilitates treatment of HIV infected mammalian cells.

The inhibition of pepsin is notable. Catalytically inert porcine pepsinogen is converted to enzymatically active pepsin by loss of the first 44 N-terminal residues (Dunn, B. M., et al. (1978), *J. Biol. Chem.* 253:7269–7276). The precursor is activated to pepsinogen by an intramolecular cleavage event. Sequence analysis of the "pro" segment amino acids reveals the porcine pepsinogen sequence: Leu-Arg-Gln-Asn-Leu at residues 12–16. Comparison of this sequence with the TF peptide inhibitors underscores the importance of the acidic residues (Glu and Asp) in the TF peptide octomer sequence: Phe-Leu-Arg-Glu-Asp-Leu-Ala-Phe (SEQ ID NO: 1). Substitution of the acidic residues (Glu and Asp) with the neutral residues Gln and Asn results in a dramatic loss of inhibitory activity (see Table 2): Phe-Leu-Arg-Gln-Asn-Leu-Ala-Phe (SEQ ID NO: 18).

Thus, some of the TF inhibitor peptides may have some general inhibitory activity against mammalian proteases, such as pepsin.

EXAMPLE 5

INHIBITION OF VIRUS REPLICATION

Cultures of Molt-3 and CEM cells which are CD4+ cell lines that are susceptible to HIV infection were chronically infected with a mixed population of HIV-1 virus isolates or HIV-1 IIIB. Cells were infected at a density of 1–2×10$^6$ cells/ml in 4 ml of RPMI 1640 (supplemented with 10% fetal bovine serum (FBS), 1% HEPES, 1% penicillin, 1% streptomycin). Infected cells were incubated with the appropriate concentration of the HIV-1 protease inhibitor for 2 hours in complete medium (RPMI 1640 with 10 percent fetal calf serum) at 37° C. The cells (1×10$^6$ per ml) were then centrifuged and resuspended in methionine-free medium with 1 percent dialyzed fetal calf serum and incubated for 30 minutes after which $^{35}$S-methionine was added to the cultures to a final concentration of 100 μC per ml. The cells were labeled for 30 minutes and 1 ml of the culture was centrifuged and saved for further analysis. After 30 minute pulse labeling as above, the label was chased by the addition of excess (100 fold) unlabeled methionine to the remaining cultures. One milliter was withdrawn after 1, 2 and 4 hours from the culture and centrifuged to separate the cells and the medium. The cell pellet was solubilized by the addition of 1 ml of the PBS-TD buffer (PBS containing 0.5% Triton X-100 and 1% deoxycholate). After 10 minutes in ice the sample was centrifuged at 12000 rpm in an Eppendorf centrifuge and the supernatant was used for radioimmunoprecipitation assay ("RIPA"). The labeled cell-free medium was solubilized by the addition of 2× PBS-TDS buffer. One ml of the solubilized medium and 0.5 ml the cell extract was made to a final volume of 1 ml with PBS-TD buffer and incubated at room temperature with 10 μl of normal human serum and 150 μl of 10% Protein A Sepharose for one hour. The sample was centrifuged at 12K rpm for two minutes. One ml of the supernatant was incubated with 10 μl of HIV-1 antibody positive human serum and 150 μl of Protein A Sepharose for two hours at room temperature. The samples were centrifuged and the Sepharose pellet was washed three times with PBS-TD buffer. The pellet was boiled for two minutes with 100 μl buffer containing 2% SDS, 2% 2-mercaptoethanol, 10 mM Tris-HCl pH 6.8 and 15% glycerol. The sample was centrifuged and the labeled proteins in the supernatant were separated in a 10% SDS-PAGE gel, treated with Amplify dried and exposed to X-ray film.

TF peptide inhibitors, EDL (SEQ ID NO: 4) or FLRED-LAF (SEQ ID NO: 1) were prepared in 200 mM or "blank" (no inhibitor) stock solutions. 1/25 to 1/200 dilutions were added to infected cultures in 1–5 ml. Final concentrations of TF peptide inhibitors were 1–8 mM.

EDL, at a concentration of 2 mM resulted in a reduction of Gag processing by 50% in cell-extracted samples and a reduction of 70% in supernatant samples, as determined by autoradiography of the p24 band.

EXAMPLE 6

USE OF TF INHIBITOR PEPTIDE TO SCREEN FOR INHIBITORS OF HIV PROTEASE

HIV protease is prepared as described, and complexed with labelled ("tagged") TF peptide or peptide cocktail, most preferably containing Glu-Asp-Leu (SEQ ID NO: 4) three amino acid inhibitor peptide. The complex is prepared under the same conditions used for the protease activity assay described above. Equimolar amounts of a labelled TF peptide and enzyme are used. Wells of 96-well microtiter plates are coated with the protease-TF inhibitor peptide(s) complex. The wells are then washed three times with phosphate buffered saline (PBS). Samples of the PBS wash are taken and assayed for the presence of unbound, labelled protease-TF peptide complex.

A test compound is then added to the wells. One or more concentrations of the test compound are typically used because the test compound is of unknown activity. Typically, concentrations are in 10-fold dilutions ranging from 10 ng to 0.1 mg concentrations. The 96-well format of the test kit makes such dilution testing convenient and reduces the rate of both false positive "hits" and false negatives. The bound complex-test inhibitor mixture is incubated for 1 hour to overnight at room temperature 37° C. The temperature and period of incubation may vary depending on the length and charge of the particular peptides in the cocktail-complex and with the properties of a particular test compound. Aliquots of 10 μl are taken from the wells at time points after addition of the test compound to the well. The aliquot is assayed for the presence of displaced, "tagged" TF peptide by described methods that are dependent on the label.

In this way, any complex that is released following addition of the test compound is distinguished from displaced "tagged" TF inhibitor peptide. Appropriate controls are used in which a "negative", compound-less buffer is added to the well, and a "positive", unlabelled TF peptide is added to the well. Release of labelled TF inhibitor peptide (above background controls) following addition of the test compound indicates a high affinity of the test compound for the protease. Compounds discovered by this screen may then be tested directly for anti-protease activity as described in the examples above.

EXAMPLE 7

ANTI-TF INHIBITOR ANTIBODIES

Peptides were prepared at 1 mg/ml having the sequence:
Cys-Gly-Gly-Gly-Gly-Gly-Phe-Leu-Arg-Glu-Asp-Leu-Ala-Phe-OH
and
Cys-Gly-Gly-Gly-Gly-Gly-Glu-Asp-Leu-Ala-Phe-OH.

Pre-bled NZW rabbits were inoculated intradermally with a mixture of 1.0 ml of peptide (500 μg) and 1.0 ml of Freunds complete adjuvant (FCA) and subcutaneously with a mixture of 0.5 to 1.0 ml of peptide (250 μg) and 1.0 ml of Freunds incomplete adjuvant (FIA). Two rabbits were inoculated with each peptide preparation. The rabbits were boosted at approximately one month intervals for 3–6 months with test bleed samples taken at each inoculation. Production bleeds, antibody preparation and analysis are performed as described (*Current Protocols in Molecular Biology*, Ausubel, F. M, ed John Wiley & Sons, Inc, 1994).

EXAMPLE 8

USE OF ANTI-TFP ANTIBODIES TO INHIBIT PROTEASE ACTIVITY

Anti-TFP antibodies generated against the TF inhibitor peptides are used to inhibit HIV protease activity in HIV-infected cells. Anti-TFP antibodies are incubated directly in virus-infected cultures of susceptible cells including primary blood mononuclear cells (PBMNC) primary cells, and transformed cell lines such as H9, Molt-3, CEM, HeLa-CD4, and U-937 cells. The cells are grown in 0.2 to 5.0 ml or more of RPMI 1640 (supplemented with 10% fetal bovine serum (FBS), 1% HEPES, 1% penicillin, 1% streptomycin) in a tissue culture flask and incubated at 37° C. The cells are infected at an optimal cell concentration of about $1–2 \times 10^6$ cells per ml. HIV-1 virus isolates are used to infect the cells at a multiplicity of infection (MOI) of 0.001 to 0.10, followed by incubation at 37° C. Anti-TFP antibodies are added to the media either directly before, concurrent with, or immediately after virus infection. Conditions vary for antibodies raised against different peptides due to the different lengths and charges of the inhibitory peptides. Both positive and negative controls are always performed, wherein some cultures are infected with "mock" solution in which no virus is present. Other cultures receive treatment of a solution in which no antibody is present. Virus activity is monitored over time by reverse transcriptase (RT) assay and P24 assay as described Kageyama, S. et al. (1994), *AIDS Res. and Human Retroviruses*, 10:735–745, in order to show inhibition of virus activity by anti-TF antibody.

EXAMPLE 9

STABILIZATION OF VIRUS USING TF INHIBITOR PEPTIDE(S)

The TF peptides are used to stabilize a virus preparation by inhibiting protease maturation, protease activity and virus autocatalysis.

TF inhibitory peptides are added to a virus preparation including that of a live vaccine.

Susceptible cells are infected with HIV-1 as described above. Infected cultures are monitored by RT assay for peak activity. Infected cells are centrifuged at 4° C. for 10 minutes at 5,000 rpm and supernatants are collected. Virus is purified by ultracentrifugation through a sucrose gradient. Purified virus is resuspended in an appropriated buffer or in water supplemented with 0.1 mM to 100 mM of TF peptide inhibitor. Conditions may vary somewhat for different peptides due to different charge and length. Each preparation is subjected to a pilot analysis in order to optimize stabilization conditions. Virus titer protease activity is measured as described at 0° C. and 37° C. in samples containing the TF peptide and in samples not containing the TF peptide.

The loss of virus activity when the virus preparation involves a live virus, such as in a live, attenuated virus vaccine, is measured as a loss of virus titer of about 0.3 log 10 after two days and 0.7 log 10 after 1 week at 37° C. The attenuated virus vaccine contains liquid or lyophilized virus, partially hydrolyzed gelatin, alcohol, cell culture medium, acceptable buffer to proper pH and either supplemented or devoid of TF peptides.

EXAMPLE 10

STRUCTURAL ANALYSIS USING TF PEPTIDE INHIBITOR

A TF peptide inhibitor is used to form crystals in complex with the HIV protease. Such crystal complexes allow for detailed three dimensional structural studies using X-ray crystallography and nuclear magnetic resonance ("NMR") studies critical for the rational design of novel inhibitors of polyprotein maturation.

Wild-type HIV-1 protease undergoes autolysis in 2 hours at room temperature, resulting in the loss of enzymatic activity even at very low protein concentrations (1–3 μM). This has hampered biophysical studies of the enzyme in the absence of inhibitors or in complex with substrate analogs with high $K_i$. To enable such analysis (including NMR and X-ray crystallography), a fully active protease variant was isolated that contains substitution mutations at potential sites of autolysis in the protease (A. Mildner et al. (1994), *J. Biol. Chem.* 33, 9405). This mutant protease which is kinetically indistinguishable from the mature protease was incubated at high protein concentrations (300–330 μM) for up to 5 days at room temperature without any loss of catalytic activity. Biophysical and kinetic analyses were performed as described (see Wondrak, E. M., et al. (1994), *J. Biol. Chem.* 269:21948–21950; and Wondrak, E. M., et al. (submitted 1995), *J. Biol. Chem.*) and indicated that substitution of the native sequences flanking the N-terminus of the protease with non-native sequences decreases the dimer stability of the protease. The purified fusion protein, containing 28 non-native amino acids fused to the N-terminus of the protease showed a $K_d$ of 200–250 mM. This value is 40 times greater than that of the mature protease. An increase in the length of sequence flanking the protease also decreases the conformational stability of the protease.

A 3–10 fold molar excess of the TFP to HIV-1 protease enzyme complex is prepared at 6 mg/ml in a buffer containing: (no salt, 0.1M Na Hepes (pH 7.5), 1.6 Na, K Phosphate) or (No salt, 0.1 Na Acetate (pH 4.6), 2.0M Na Formate) or (No Salt, 0.1M Tris HCl (pH 8.5), 2.0M $NH_4$ Phosphate) or (30% w/v polyethylene glycol ("PEG") monomethylether 2000, 0.1M Sodium Acetate (pH 4.6), 0.2M Ammonium sulfate). See Gorman, M. A., et al. (1992), *J. Mol. Biol.,* 228:991–994; Erickson, J., et al. (1990), *Science,* 249:527–533; Abdel-Megiud, S. S., et al. (1993), *Biochem.,* 32:7972–7980.

The complex is prepared, crystalized, and analyzed as described (Tong, L., et al. (1993), *Proc. Natl. Acad. Sci. USA* 90:8387–8391; Harrison, R. W., and Weber, I. T. (1994), *Protein Engineering* 7:1353–1363). X-ray diffraction and NMR analyses are performed in order to elucidate the interactions between the TF peptide inhibitor and its analogs and the HIV protease, thereby enabling the design of novel potent inhibitors.

EXAMPLE 11

INHIBITION OF HIV-1-MEDIATED HYDROLYSIS OF SYNTHETIC SUBSTRATES BY TF PEPTIDE INHIBITOR(S)

Reactions were performed in a total volume of 10 μl in 50 mM sodium acetate, pH 5.0 or 100 mM sodium phosphate at pH 5.5 containing 1 mM DTT, 1 mM EDTA, 1M NaCl, in the presence of test substrate and 0.7 to 0.8 μM mature HIV-1 protease and incubated at 37° C. Reactions were terminated with 190 μl of a solution of 8M guanidine hydrochloride and 1% trifluroacetic acid (TFA) and subjected to reverse-phase high performance liquid chromotography ("RP-HPLC") on a $C_{18}$ column. The substrate and cleavage products were separated with a linear gradient of 0 to 50% acetonitrile in water containing 0.05% TFA. The identity of the cleavage products was confirmed by electrospray mass spectroscopy. Peak areas were integrated using the Turbochrom 4 software (Perkin Elmer, San Jose, Calif.). Lineweaver-Burk analysis was used to determine $k_{cat}$ and $K_m$.

It is significant to note that the TF region is flanked by sequences that form substrates for the viral protease. The viral protease catalyzes the hydrolysis of the synthetic peptide spanning the TFP/TFp6 junction sequence. The $k_{cat}/K_m$ for the hydrolysis of the substrate corresponding to the TFP/TFp6 cleavage site is quite similar to the hydrolysis of a substrate spanning the TFp6/protease cleavage site (see Table 1). A polyprotein composed of the p7 and p1 domains of the Gag precursor is cleaved by the protease between p7 and p1 at about the same efficiency as that of the substrate encompassing the TFP/TFp6 cleavage site (Wondrak et. al. (1993), *FEBS lett.* 333:21–24). But, in the Gag-Pol polyprotein, the p7/TFP junction is different in its sequence in the carboxyl side P3' and P4' position, amino acids, involved in substrate specificity. A synthetic peptide spanning this p7/TFP cleavage site, Glu-Arg-Gln-Ala-Asn-Phe-Leu-Arg-Glu-Asp (substrate III), was hydrolysed far less efficiently than the substrate corresponding to the TFP/TFp6 cleavage site, Asp-Leu-Ala-Phe-Leu-Gln-Gly-Lys (substrate IV) (See Table 1). The products Phe-Leu-Arg-Glu-Asp and Asp-Leu-Ala-Phe derived by the hydrolysis of substrates III and IV, respectively, were isolated by RP-HPLC and confirmed by electrospray mass spectrometry (M/z=695.4 and 465.2 respectively). Provided that the p7/TFP site is cleaved during virus maturation, TF peptides in principle represent P4'-P4 (Glu-Asp) fusion of two half substrates and will be the smaller of the proteolytic products of the Gag-Pol polyprotein in comparison to the Gag derived p1 and p2 proteins. Peptide substrates III and IV show inhibition of protease catalyzed hydrolysis of these substrates at lower pHs.

We claim:

1. A peptide consisting of at least one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17.

2. A method of screening a test compound for antiretroviral activity comprising:

contacting said test compound with a retroviral protease complexed with a peptide of claim 1; and detecting displacement of said peptide with said compound; and assaying said compound for inhibition of protease activity.

3. The method of claim 2 wherein said peptide is labelled.

4. The method of claim 2 wherein the viral protease is immobilized onto a solid matrix.

5. A test kit for screening a test compound inhibitory of aspartyl proteases comprising:

a. a peptide according to claim 1; and b. an aspartyl protease.

6. The test kit of claim 5 further comprising a solid support.

7. The test kit of claim 5 further comprising:

a negative control sample in which no protease or inactive protease is present; and a positive control sample in which protease with known activity is present.

8. A method of stabilizing a retroviral preparation comprising the step of: supplementing the retroviral preparation with at least one peptide of claim 1.

9. An antibody reactive with at least one peptide of claim 1.

10. An anti-idiotypic antibody reactive with the antibody of claim 9.

* * * * *